United States Patent
Rideout

(10) Patent No.: US 8,480,710 B2
(45) Date of Patent: Jul. 9, 2013

(54) WOUND CLOSURE DEVICE INCLUDING SUCTION STEP SLEEVE

(75) Inventor: Christina Rideout, Middletown, CT (US)

(73) Assignee: Covidien LP, Mansfield, MA (US)

( * ) Notice: Subject to any disclaimer, the term of this patent is extended or adjusted under 35 U.S.C. 154(b) by 168 days.

(21) Appl. No.: 12/939,493

(22) Filed: Nov. 4, 2010

(65) Prior Publication Data
US 2012/0116445 A1    May 10, 2012

(51) Int. Cl.
*A61B 17/08* (2006.01)

(52) U.S. Cl.
USPC ............ 606/216; 606/157; 606/191; 606/213

(58) Field of Classification Search
USPC ................................. 606/213–216
See application file for complete search history.

(56) References Cited

U.S. PATENT DOCUMENTS

| | | | |
|---|---|---|---|
| 5,183,464 A | 2/1993 | Dubrul et al. | |
| 5,814,058 A | 9/1998 | Carlson et al. | |
| 5,827,319 A | 10/1998 | Carlson et al. | |
| 5,891,111 A | 4/1999 | Ismael | |
| 6,626,930 B1 * | 9/2003 | Allen et al. | 606/213 |
| 2004/0092960 A1 * | 5/2004 | Abrams et al. | 606/139 |
| 2004/0116897 A1 | 6/2004 | Aboul-Hosn | |
| 2005/0065484 A1 | 3/2005 | Watson, Jr. | |
| 2005/0119652 A1 * | 6/2005 | Vetter et al. | 606/45 |
| 2005/0171470 A1 | 8/2005 | Kucklick et al. | |
| 2006/0041247 A1 * | 2/2006 | Petrosenko et al. | 604/543 |
| 2006/0259027 A1 * | 11/2006 | Kwan et al. | 606/41 |
| 2007/0123851 A1 * | 5/2007 | Alejandro et al. | 606/45 |
| 2010/0191279 A1 * | 7/2010 | Kassab et al. | 606/213 |
| 2011/0066000 A1 | 3/2011 | Ibrahim et al. | |

OTHER PUBLICATIONS

European Search Report for EP 11250798.3-2310 date of completion is Jan. 31, 2012 (3 pages).

* cited by examiner

*Primary Examiner* — Corrine M McDermott
*Assistant Examiner* — Alexander Orkin

(57) ABSTRACT

An access apparatus is adapted and configured to access an underlying body cavity. The access apparatus includes a sleeve including a plurality of tubules. The tubules are configured and adapted to suction fascia of opposing tissue tracts to facilitate wound closure. A method of using the access apparatus is also provided.

10 Claims, 6 Drawing Sheets sleeve applies suction to draw wound closed sleeve applies suction
to draw wound closed sleeve inserted in wound

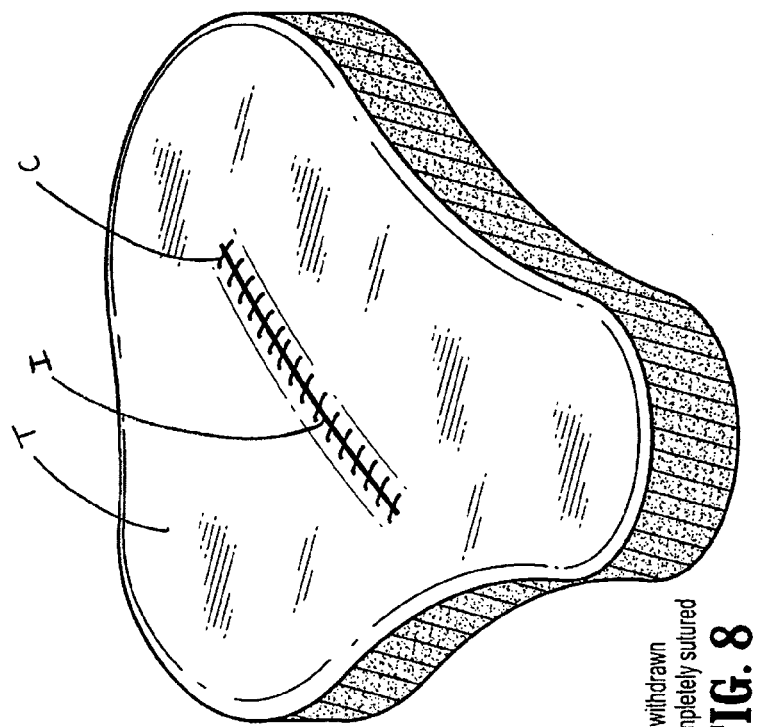
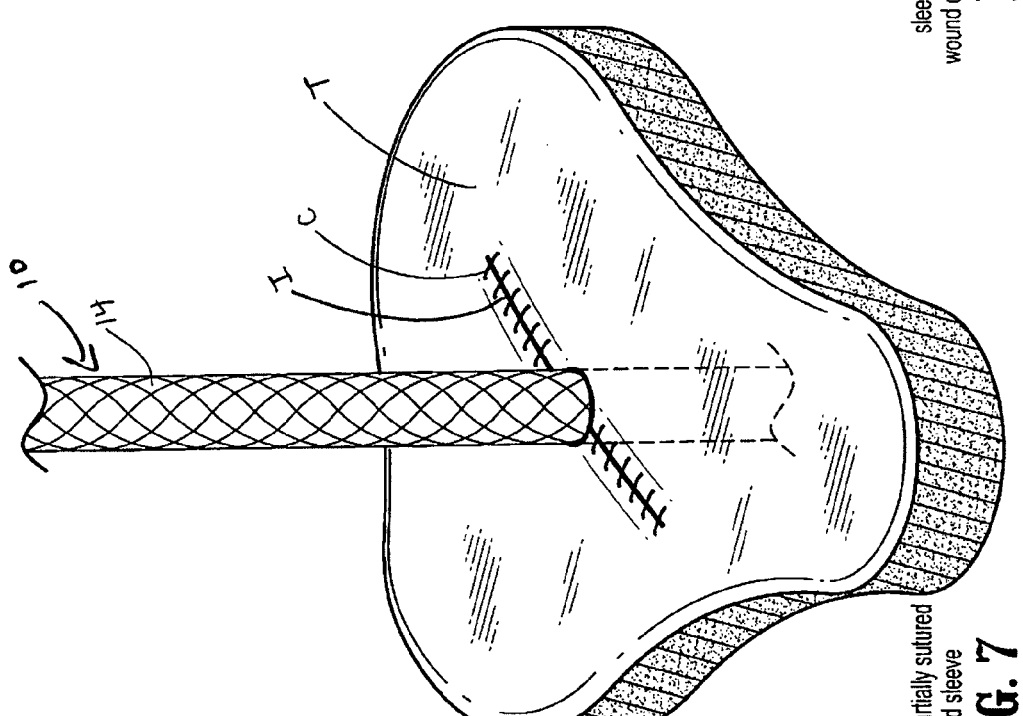
FIG. 7 wound partially sutured around sleeve
FIG. 8 sleeve withdrawn wound completely sutured

WOUND CLOSURE DEVICE INCLUDING SUCTION STEP SLEEVE

BACKGROUND

1. Technical Field

The present disclosure relates to a method and to an apparatus for facilitating wound closure. More particularly, the present disclosure relates to a device that facilitates closure and/or fixation of the wound.

2. Background of Related Art

Minimally invasive surgery, e.g., laparoscopic, endoscopic, and thoroscopic surgery, has become increasingly popular in recent years. Minimally invasive surgery eliminates the need to cut a large incision in a patient, thereby reducing discomfort, recovery time, and many of the deleterious side effects associated with traditional open surgery.

The initial puncture is usually very small so that a needle or trocar can achieve the desired penetration without excessive damage to tissue. It may be necessary for the initial access hole to be subsequently enlarged to provide a working diameter to permit introduction of surgical instruments and the performance of the desired medical procedure.

Complications with having a larger access hole include leakage of body fluids and substances through the enlarged opening. Moreover, body structures that are being penetrated frequently comprise relatively flaccid membranes or walls such that penetration with a larger sized dilator may result in fascial detachment, i.e., the invagination and separation of the membrane or wall from surrounding tissue structures. Such problems may be exacerbated when the organ, tissue, or cavity being penetrated is diseased such that the membranes or walls are thickened or toughened and resistant to penetration by the dilator that axially engages the tissue.

Various devices and techniques have been developed to provide an enlarged opening while minimizing the negative consequences of having an enlarged opening. One approach for preventing fascial detachment of the internal body organ or structure during the dilation process involves the use of separate anchoring instruments that are placed around the site of penetration and dilation. The technique relies on the placement of multiple separate anchors or toggles peripherally about the site of the primary puncture in order to more strongly attach the body organ to its surrounding fascia. The anchors are attached to lengths of suture that extend through the tracks defined by the separate punctures. The sutures are tensioned in order to hold the wall of the hollow organ against the fascia and subsequently secured outside the body. This approach requires a separate puncture for each anchor and the subsequent suturing of each anchor in place. The technique is therefore relatively time consuming, costly, and subjects the patient to discomfort from the creation of multiple puncture wounds.

A radially expandable access system has become commercially available under the trademark STEP™ and is owned by the assignee of the present application. Certain aspects of the STEP™ access system are described in U.S. Pat. Nos. 5,183,465; 5,431,676; 5,814,058; and 5,827,319, which are assigned to the assignee of the present applications, the contents of which are hereby incorporated by reference herein.

The STEP™ access system includes a pneumoperitoneum needle, an expandable sleeve component which is percutaneously introduced while positioned over the pneumoperitoneum needle, a cannula having a pneumostasis valve permanently affixed at its proximal end, and an obturator which is removably inserted into the cannula. After the needle/sleeve assembly has been percutaneously introduced, and the peritoneal cavity insufflated in the case of laparoscopic procedures, the needle is removed from the sleeve, and the cannula/obturator assembly introduced through the sleeve. The sleeve, which initially has a diameter in the range of 2-3 mm, is expanded by the cannula and obturator to a final diameter which can be selected from 5 mm, 10 mm, or 12 mm. Use of the STEP™ access system facilitates the replacement of the cannula with a larger diameter cannula through a previously introduced sleeve.

After completion of the desired procedure, the instruments used for the procedure including the sleeve are removed, and the wound is sutured closed. A continuing need exists for improved devices and methods for closure of wounds formed to facilitate insertion of access systems.

SUMMARY

The present disclosure describes an apparatus for accessing an underlying body cavity and for facilitating closure of the wound into which the apparatus is placed. The apparatus may include a radially expandable sleeve including a first axial lumen therethrough and an outer surface. A cannula is disposed within the first axial lumen of the sleeve and includes a second axial lumen through which an instrument, e.g., an obturator, is removably receivable.

A plurality of tubules is positioned about the outer surface of the sleeve such that the tubules are in position to apply suction to the tissue fascia to facilitate wound closure. The tubules are configured and adapted to apply suction to the fascia of tissue adjacent to a wound or incision in which the apparatus is inserted. The tubules may be woven together or may be interlaced within a mesh. The tubules may be incorporated into a mesh sheath and run axially to the distal end of the sheath, i.e., the tubules are vertically oriented when the sheath is in the cavity. Each of the tubules may be operably coupled to a central source of suction. The tubules may also or alternatively be sewn, glued, heated, or ultrasound welded to one another.

The suction applied by the tubules gathers the fascia together to facilitate wound closure. The sleeve is released from the wound by removing the source of suction from the tubules once the fascia is sutured, whereafter the fascia are no longer held together by suction. In an embodiment, some or all of the tubules may also be configured to dispense a substance, e.g., an adhesive or a glue. An adhesive or a glue may facilitate maintaining the fascia of the tissue in a closed or an approximated position.

Also described herein is a method of closing a wound including the step of placing a wound closure device, such as that described above, within a wound within a tissue. The wound closure device is configured and adapted to apply a suction force to the fascia of the wound to approximate the wound about the wound closure device. As described above, the wound closure device includes a sleeve including a plurality of tubules disposed along the length of the sleeve. Each of the tubules is configured and adapted to apply a suction force. Upon application of the suction force, the fascia of the tissue near or adjacent the sleeve are drawn together. The tissue that has been drawn together may now be closed, .e.g., stapled or sutured, around the sleeve. Thereafter, the wound closure device, including the sleeve, is removed and the unclosed portion of the wound is closed, e.g., stapled or sutured.

These and other features of the present disclosure will be more fully described below with reference to the appended figures.

BRIEF DESCRIPTION OF THE DRAWINGS

By way of description only, embodiments of the disclosure will be described with reference to the accompanying drawings, in which:

FIG. 7 is a perspective view of the access apparatus of FIG. 1, as shown in FIG. 5, with the wound partially sutured around the access apparatus; and FIG. 8 is a perspective view of the wound, as shown in FIG. 5, completely sutured.

DETAILED DESCRIPTION

Figure 1:
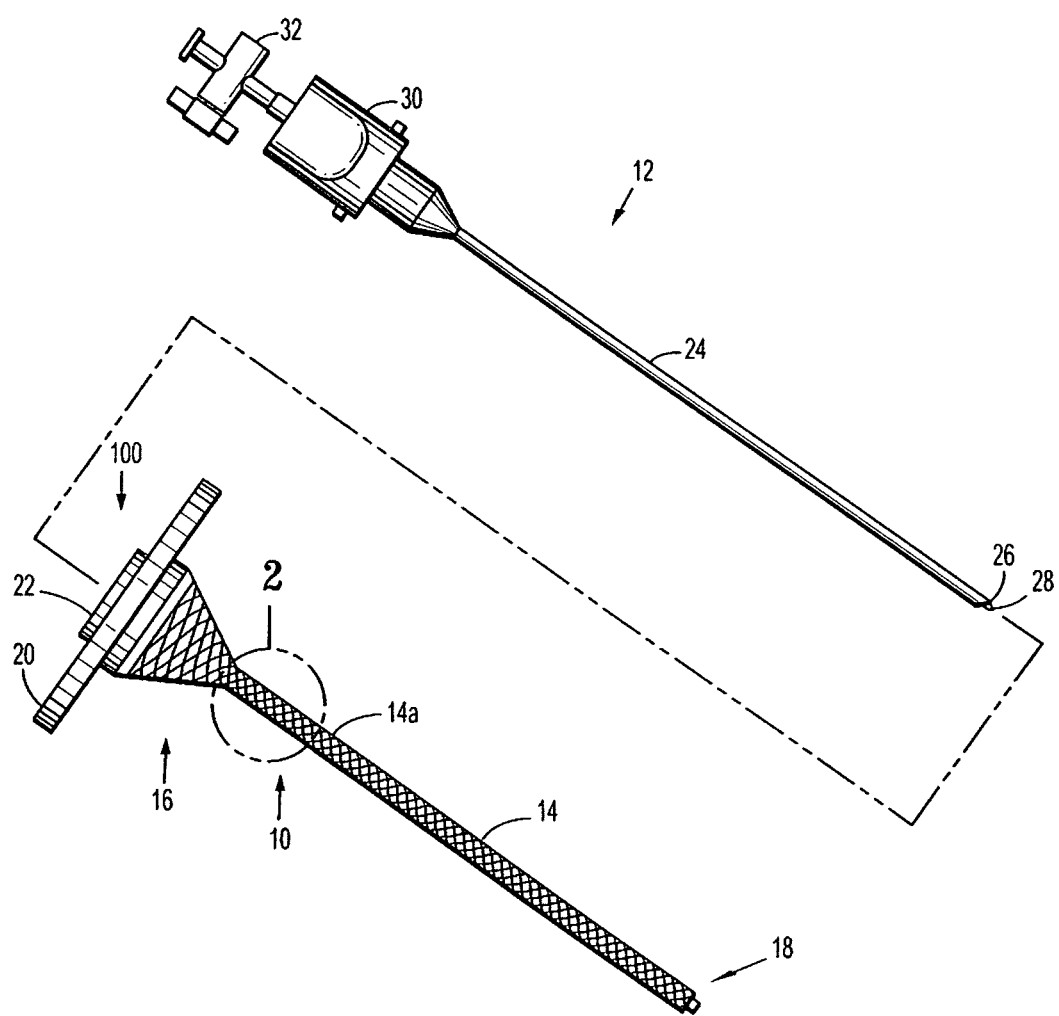
FIG. 1 is a front view of an access apparatus shown relative to a pneumo-peritoneum needle.

Particular embodiments of the present disclosure will be described herein with reference to the accompanying drawings. As shown in the drawings and as described throughout the following descriptions, and is traditional when referring to relative positioning on an object, the term "proximal" refers to the end of the apparatus that is closer to the user and the term "distal" refers to the end of the apparatus that is further from the user. In the following description, well-known functions or constructions are not described in detail to avoid obscuring the present disclosure in unnecessary detail.

An access apparatus 100 will now be described with reference to FIGS. 1-4. As shown in FIG. 1, the access apparatus 100 includes a sleeve 10 that includes a radially expandable tube 14 including proximal region 16 and a distal region 18. The proximal region 16 may taper distally such that the diameter of the tube 14 narrows from the proximal end to the distal end of the proximal region 16. The tapering of the proximal region 16 facilitates insertion of instrumentation through a lumen extending through the central longitudinal axis of the tube 14.

In addition, a handle 20 may be secured to the proximal region 16. The handle 20 includes an aperture (not shown) that is aligned with the diameter of the proximal region 16. A bayonet fitting 22 is aligned with the aperture and facilitates reception of an instrument into the aperture and securing of the instrument to the handle 20. The instrument that is secured to the handle 20 may include a pneumo-peritoneum needle 12, as is shown in FIG. 1.

The pneumo-peritoneum needle 12 may be placed within a lumen (not shown) of the sleeve 10 to facilitate insufflation of the body cavity. A bayonet fitting 30 is disposed at a proximal end of the hypotube shaft 24. The bayonet fitting 30 of the hypotube shaft 24 cooperates with the bayonet fitting of the handle 20 to facilitate securing the pneumo-peritoneum needle 12 to the handle 20. A valve 32 is positioned proximal to the fitting 30, and may be connected to a source of insufflation gasses. Securing the bayonet fitting 30 of the hypotube shaft 24 to the bayonet fitting 22 of the handle 20 may be accomplished by placing the bayonet fitting 30 adjacent the bayonet fitting 22 and rotating one relative to the other.

The pneumo-peritoneum needle 12 includes a hypotube shaft 24 including a sharpened distal tip 26 and a spring loaded obturator 28 extending from the distal tip 26. The sharpened tip 26 and the obturator 28 of the needle 12 extends distally from the distal region 18 of the conformable sleeve 10. In this way, the assembly of the sleeve 10 and the needle 12 may be directly introduced through a patient's skin (i.e., without needing a prior penetration) to form a percutaneous penetration of the target body cavity.

After initial penetration, the peritoneum needle 12 may be used to provide for initial insufflation of the patient's body cavity, typically the abdomen for laparoscopic procedures. Often, however, the sleeve 10 will be introduced in non-laparoscopic procedures and/or after the procedure has begun. In such cases, the use of a peritoneum needle is not required. A simpler needle or insertion device could be used in such circumstances, but inclusion of the obturator 28 is advantageous since it reduces the risk of injury from blind insertion of an unprotected needle tip.

Figure 3:
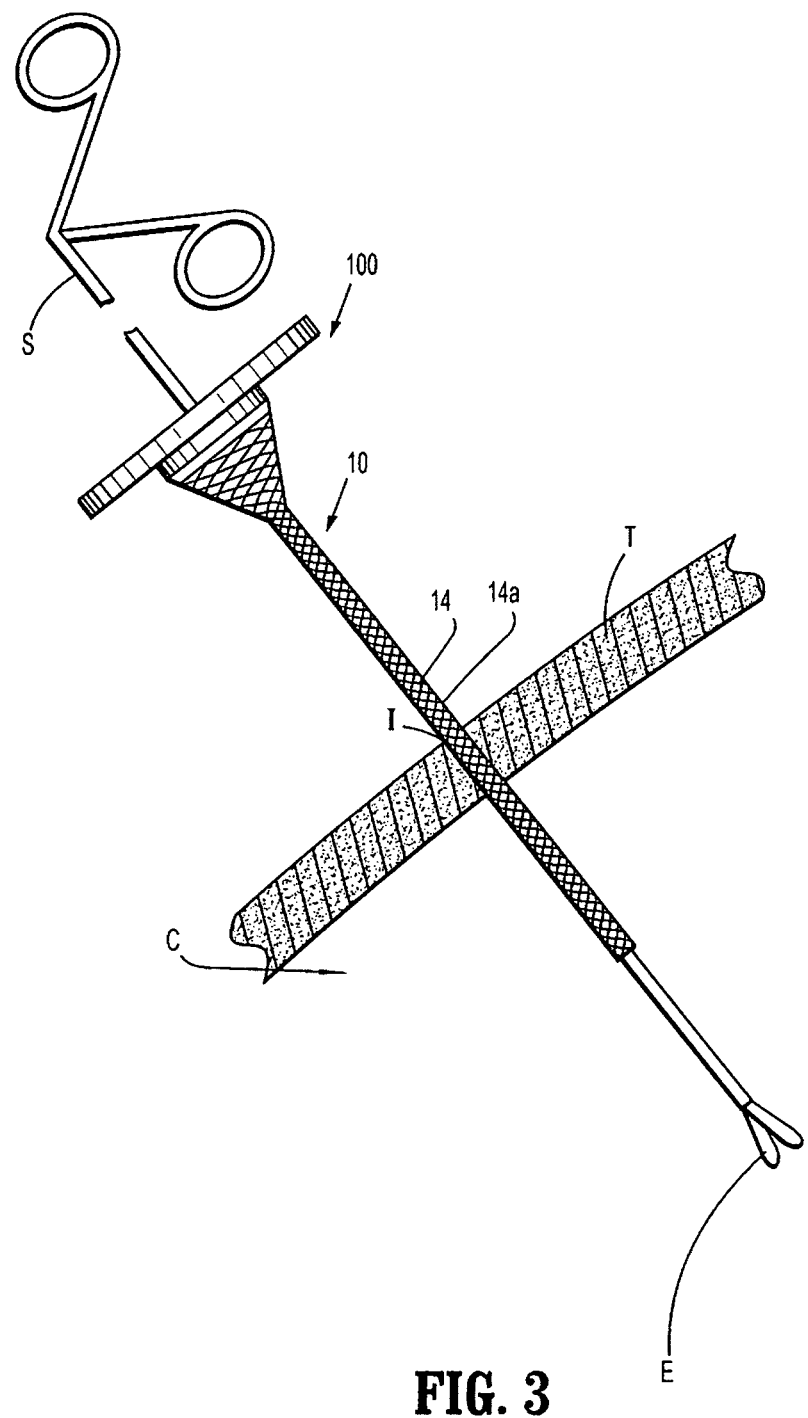
FIG. 3 is a front view of the access apparatus of FIG. 1 shown in a first state, placed within a tract of tissue, and having a surgical instrument inserted within the access apparatus.
Figure 4:
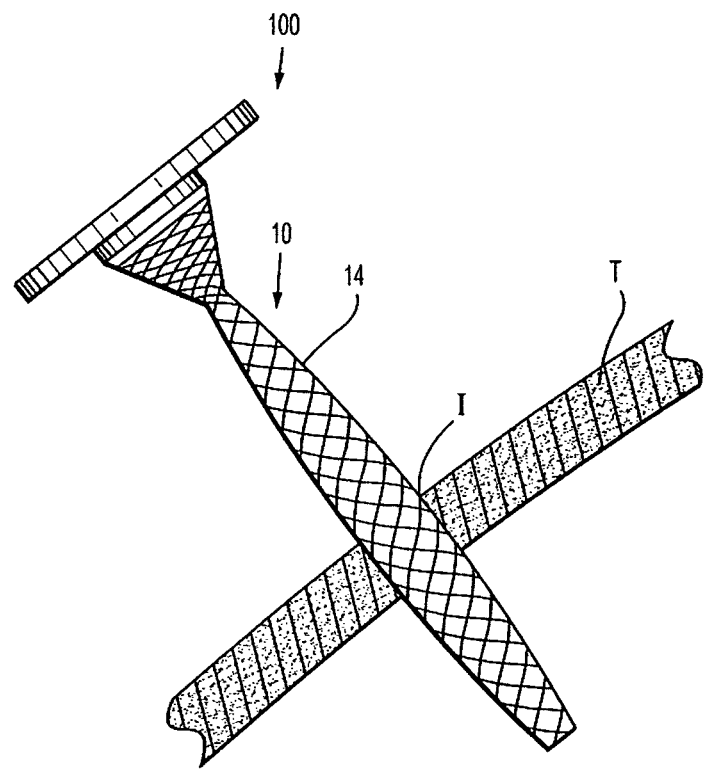
FIG. 4 is a front view of the access apparatus of FIG. 1 shown in a second state and placed within a tract of tissue.

As seen in FIGS. 3-4, the tube 14 may be radially expandable from a resting or a first state (FIG. 3) to an expanded or a second state (FIG. 4) to substantially fill a gap between tissue portions T and/or to expand the size of an incision I. The tube 14 may transition to the expanded state in response to a larger sized diameter instrument being placed within the lumen of the tube 14. Insertion of larger sized diameter instruments into the lumen of the tube 14 and the corresponding expansion of the tube 14 may also increase the size of the wound I within tissue T.

The radially expandable tube 14 of the sleeve 10 may comprise a braided material covered by an elastic membrane to form a mesh 14a. In some embodiments, the tube 14 may be formed from an expandable elastic material. Moreover, the mesh 14a may be configured and adapted to expand as objects or instruments pass through the sleeve 10, and will radially close upon removal of the objects or instruments from the elastic force of the membrane. As shown in FIG. 3, a surgical instrument S including an end effector E may be introduced through the tube 14 of the sleeve 10 into the body cavity C.

Figure 2:
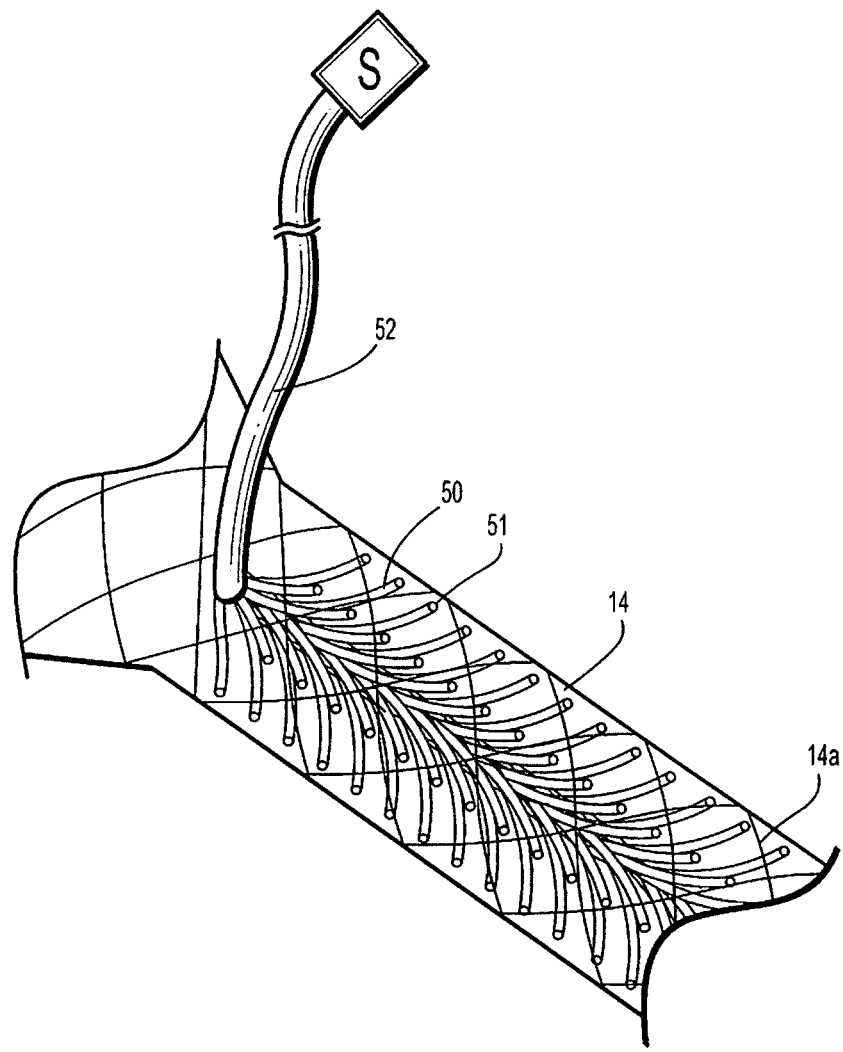
FIG. 2 is an enlarged view of the indicated area of FIG. 1 shown connected to a source of suction.

Moreover, as shown in FIG. 2, a plurality of tubules 50 may be disposed along the length of the tube 14. For example, the tubules 50 may be glued, bonded, ultrasound welded, heated, sewn or woven together, or interlaced within the mesh 14a of the tubular sheath 14 such that a plurality of tubules 50 are positioned along the length of the tube 14 and extend through the mesh 14a. The tubules 50 are configured and adapted to apply suction to the fascia of tissue T adjacent to a wound or incision I in which the apparatus 100 is inserted. The tubules 50 may run axially to the proximal region 18 of the sheath 14, i.e., the tubules 50 are vertically oriented when the sheath 14 is in the cavity C. The tubules 50 may terminate at different points along the length of the sheath 14 to facilitate suction of tissue T along the length of the sheath 14 inserted between the portions of the tissue T.

In some embodiments, the tubules 50 may form a braided material or may be incorporated within a braided material. In still other embodiments, the tubules 50 form a woven material that may form an expandable tube or are otherwise operably coupled to an expandable tube or braid. In each of these embodiments, an outer membrane or covering may or may not be used.

As shown in FIG. 2, each of the tubules 50 may be connected to a common tubule 52 that is connected to a source S (FIG. 2) of suction. The suction applied by the tubules 50 gathers the fascia, and other tissue, together to facilitate wound closure. As the suction is applied, fascia in contact or near the tubular sheath 14 is drawn toward inlets 51 of the tubules 50. This creates an inwardly directed force that reduces the size of the wound I.

A method of using the access apparatus 100 will now be described. As discussed above, the tube 14 of sleeve 10 is configured and adapted to receive instruments, e.g., needle 12, therein. In response to the dimensions of such instruments, the tube 14 is configured and adapted to have a diameter that adjusts in response to the dimensions of the instrument inserted therein. Once the procedure has been completed, the access apparatus 100 may be used to facilitate closure of the wound I, as is discussed below in greater detail.

Figure 6:
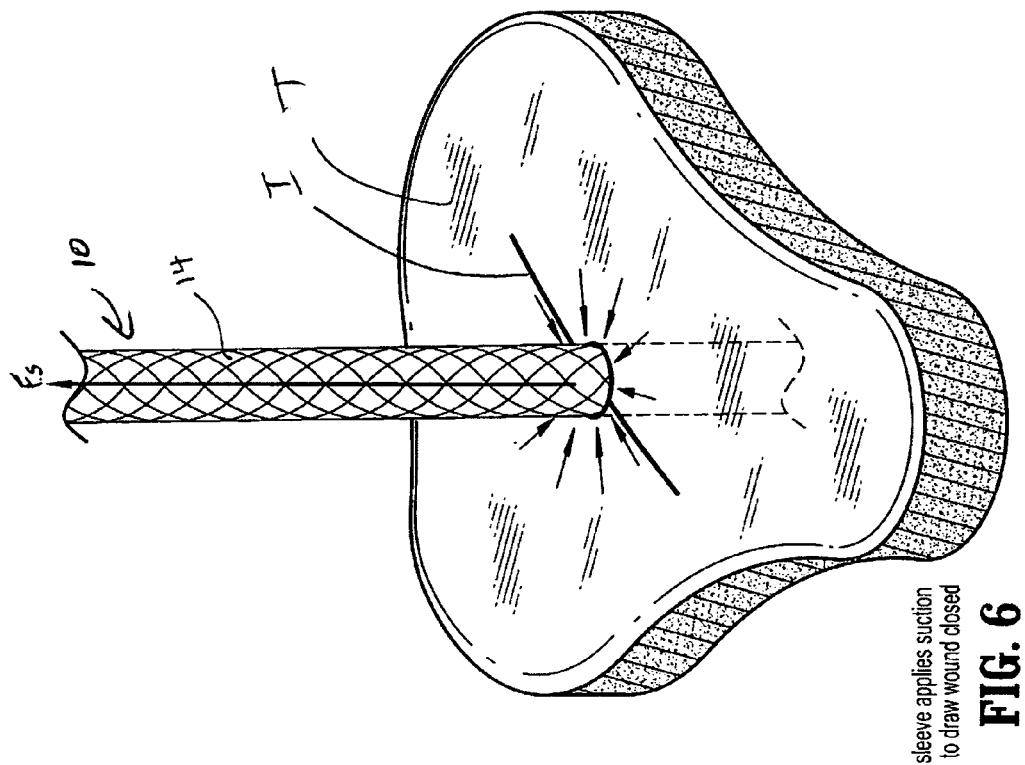
FIG. 6 is a perspective view of the access apparatus of FIG. 1, as shown in FIG. 5, with the wound being drawn closed.
Figure 5:
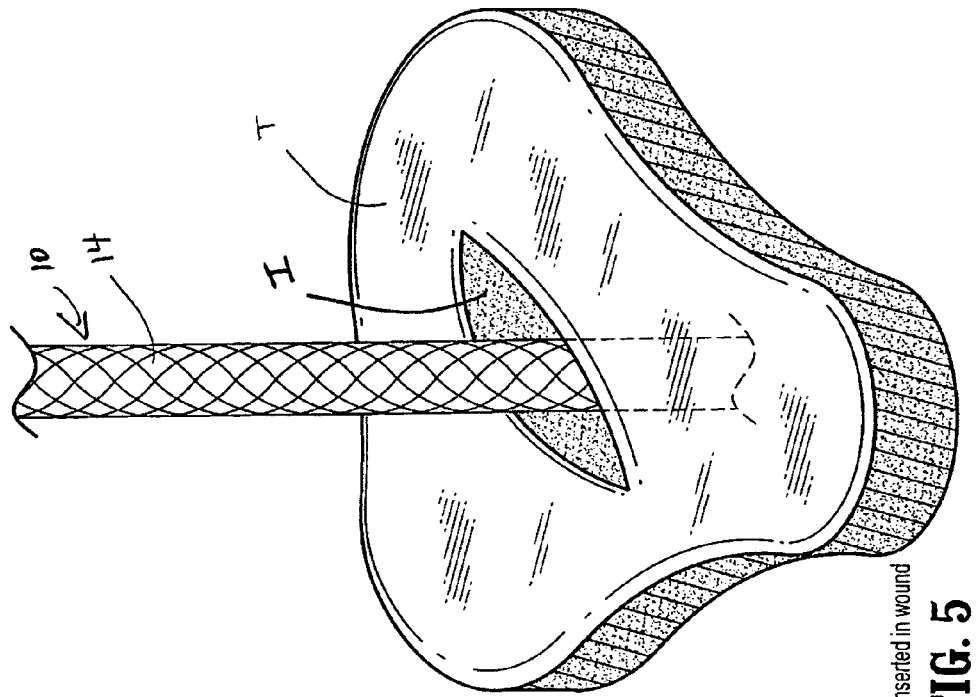
FIG. 5 is a perspective view of the access apparatus of FIG. 1 shown placed within an open wound.

A method of using the access apparatus to facilitate wound closure will now be described with reference to FIGS. 5-8. As shown in FIG. 5, the tube 14 of the sleeve 10 is positioned within an open wound I of tissue T. As described above, with reference to FIG. 2, disposed along the length of the tube 14 is a plurality of tubules 50, each including an inlet 51. Each of these inlets 51 is adjacent or near fascia of the tissue T within wound I. Thus, as shown in FIG. 6, upon application of a suction force Fs that is directed proximally through the common tubule 52, each of the inlets 51 directs an inward force to draw the fascia of the tissue T together. As will be discussed below, inlets 51 may be also be adapted to dispense a substance, e.g., an adhesive and/or glue.

Accordingly, the suction force Fs results in the fascia of tissue T near or adjacent the inlets 51 to be drawn together, thereby reducing the size of the wound I and closing the wound I about the tube 14. The magnitude of the suction force Fs is proportional to the diameter of the common tubule 52 and the tubules 50, i.e., the narrower the common tubule 52 and/or tubules 50, the greater the suction force Fs, and the wider the common tubule 52 and/or tubules 50, the lesser the suction force Fs.

As shown in FIG. 7, once the fascia of the tissue T are sufficiently approximated, the wound I may be partially closed about the tube 14. Closing means, as are known in the art, e.g., sutures, staples, clips, glue, or adhesive, may be used to close the wound I. As shown in FIG. 7, a length of suture C is sutured about the tube 14 to approximate the fascia of the tissue T together, thereby partially closing the wound I. Alternatively, surgical staples may be used to close the approximated fascia of tissue T. Once the wound I within the tissue T is sufficiently approximated, the tube 14 of the sleeve 10 is removed from the wound I. Thereafter, the unclosed portion of the tissue T is closed, e.g., the portion of the tissue that had not been closed since the tube 14 was still in the wound I may now be closed, e.g., sutured or stapled.

In an embodiment, some of the tubules 50 or other tubules may be configured and adapted to dispense an adhesive and/or glue to close the fascia layer of the tissue T. The skin layer of the tissue T may then be closed, for example, by staples or sutures. In an embodiment, subsequent to drawing the fascia of tissue T together (FIG. 6), the source S (FIG. 2) may be adapted to dispense an adhesive and/or glue through the tubules 50. The adhesive and/or glue may facilitate maintaining and fixating of the fascia of tissue T together.

It will be understood by those skilled in the art that various modifications and changes in form and detail may be made therein without departing from the scope and spirit of the present disclosure. Accordingly, modifications and changes in form and detail may be made therein without departing from the scope and spirit of the present disclosure.

What is claimed is:

1. A method of wound closure, comprising the steps of:
    placing a tubular sleeve within a wound of a tissue, the tubular sleeve configured to receive a surgical instrument therethrough and expand radially outward, the tubular sleeve including:
        an outer surface; and
        a plurality of tubules, the tubules positioned about the outer surface of the sleeve, each of the tubules configured and adapted to apply a radial and inwardly directed force to draw tissue positioned near the sleeve toward the sleeve;
    applying a suction to the tubules, thereby drawing the wound partially closed;
    partially approximating the wound about the sleeve;
    removing the sleeve from the wound; and
    closing the wound.

2. The method of claim 1, further comprising the step of inserting an instrument within the sleeve.

3. The method of claim 2, wherein the sleeve radially expands to accommodate the instrument.

4. The method of claim 2, wherein the sleeve has a diameter that adjusts in response to a diameter of the instrument inserted within the sleeve.

5. The method of claim 1, wherein the plurality of tubules are disposed along the length of the sleeve.

6. The method of claim 1, wherein the plurality of tubules are woven together.

7. The method of claim 1, wherein the plurality of the tubules are connected to an external source of suction.

8. The method of claim 1, wherein the tubular sleeve includes a braided material covered by an elastic membrane to form a mesh.

9. The method of claim 8, wherein the mesh is configured and adapted to expand as the surgical instrument is inserted through the tubular sleeve.

10. The method of claim 9, wherein the mesh is configured and adapted to radially close upon removal of the surgical instrument.

* * * * *